(12) United States Patent
Guo et al.

(10) Patent No.: US 11,521,323 B2
(45) Date of Patent: Dec. 6, 2022

(54) SYSTEMS AND METHODS FOR GENERATING BULLSEYE PLOTS

(71) Applicant: SHANGHAI UNITED IMAGING INTELLIGENCE CO., LTD., Shanghai (CN)

(72) Inventors: Yimo Guo, Lexington, MA (US); Xiao Chen, Lexington, MA (US); Shanhui Sun, Lexington, MA (US); Terrence Chen, Lexington, MA (US)

(73) Assignee: SHANGHAI UNITED IMAGING INTELLIGENCE CO., LTD., Shanghai (CN)

(*) Notice: Subject to any disclaimer, the term of this patent is extended or adjusted under 35 U.S.C. 154(b) by 52 days.

(21) Appl. No.: 17/076,641

(22) Filed: Oct. 21, 2020

(65) Prior Publication Data
US 2022/0122259 A1    Apr. 21, 2022

(51) Int. Cl.
*G06K 9/00* (2022.01)
*G06T 7/11* (2017.01)
(Continued)

(52) U.S. Cl.
CPC .............. *G06T 7/11* (2017.01); *A61B 5/0044* (2013.01); *A61B 5/055* (2013.01); *A61B 5/743* (2013.01); *G06K 9/6261* (2013.01); *G06T 7/74* (2017.01); *G06T 11/206* (2013.01); *G06T 2207/10088* (2013.01); *G06T 2207/20072* (2013.01);
(Continued)

(58) Field of Classification Search
CPC ........................................................ G06T 7/11
See application file for complete search history.

(56) References Cited

U.S. PATENT DOCUMENTS

| | | | |
|---|---|---|---|
| 2010/0067764 A1* | 3/2010 | Lu | G06T 7/13 382/131 |
| 2012/0232379 A1* | 9/2012 | Ionasec | G06T 7/12 600/414 |

(Continued)

OTHER PUBLICATIONS

Khalifa et al., "Automatic Analysis of Left Ventricle Wall Thickness Using Short-Axis Cine CMR Images", IEEE, 2011, pp. 1306-1309.
(Continued)

*Primary Examiner* — Oneal R Mistry
(74) *Attorney, Agent, or Firm* — Zhong Law, LLC

(57) ABSTRACT

A bullseyes plot may be generated based on cardiac magnetic resonance imaging (CMRI) to facilitate the diagnosis and treatment of heart diseases. Described herein are systems, methods, and instrumentalities associated with bullseyes plot generation. A plurality of myocardial segments may be obtained for constructing the bullseye plot based on landmark points detected in short-axis and long-axis magnetic resonance (MR) slices of the heart and by arranging the short-axis MR slices sequentially in accordance with the order in which the slices are generated during the CMRI. The sequential order of the short-axis MR slices may be determined utilizing projected locations of the short-axis MR slices on a long-axis MR slice and respective distances of the projected locations to a landmark point of the long-axis MR slice. The myocardium and/or landmark points may be identified in the short-axis and/or long-axis MR slices using artificial neural networks.

18 Claims, 8 Drawing Sheets

(51) Int. Cl.
  *A61B 5/055* (2006.01)
  *G06T 7/73* (2017.01)
  *G06K 9/62* (2022.01)
  *G06T 11/20* (2006.01)
  *A61B 5/00* (2006.01)

(52) U.S. Cl.
  CPC ............... *G06T 2207/20084* (2013.01); *G06T 2207/30048* (2013.01); *G06T 2210/41* (2013.01); *G06V 2201/031* (2022.01)

(56) References Cited

U.S. PATENT DOCUMENTS

| | | | | |
|---|---|---|---|---|
| 2013/0259337 | A1* | 10/2013 | Guhring | G06T 7/0012 |
| | | | | 382/131 |
| 2015/0153434 | A1* | 6/2015 | Ooshima | G01R 33/5676 |
| | | | | 324/309 |
| 2016/0098833 | A1* | 4/2016 | Tsadok | G06K 9/6201 |
| | | | | 382/128 |
| 2017/0071675 | A1* | 3/2017 | Dawoud | A61B 5/0035 |
| 2020/0219262 | A1* | 7/2020 | Hsiao | G06N 3/0445 |
| 2021/0142887 | A1* | 5/2021 | Gheorghita | G16H 50/20 |
| 2021/0216878 | A1* | 7/2021 | Norman | G06T 7/33 |

OTHER PUBLICATIONS

Zheng et al., "Explainable cardiac pathology classification on cine MRI with motion characterization by semi-supervised learning of apparent flow," arXiv:1811.03433v2, 2019, pp. 1-17.

Cerqueira et al., "Standardized Myocardial Segmentation and Nomenclature for Tomographic Imaging of the Heart," Journal of Cardiovascular Magnetic Resonance, 2002, pp. 1-7.

\* cited by examiner

SYSTEMS AND METHODS FOR GENERATING BULLSEYE PLOTS

BACKGROUND

Cine magnetic resonance imaging (CMRI) is a standard imaging modality for non-invasive cardiac diagnosis. Using CMRI, high-resolution and multi-slice anatomical images of the human heart may be acquired over multiple cardiac cycles during different scan or examination procedures. The CMRI data may then be integrated and presented to visualize areas of the human heart and provide an intuitive overview of the conditions of the heart including, e.g., myocardial mass, myocardial strain, wall thickness, etc. An example technique for presenting the CMRI data is by constructing a bullseye plot in which the myocardium is divided into multiple standard segments and determining quantitative and/or qualitative information such as the myocardial strain for each of the segments. Diagnosis and/or treatment may then be performed by referencing to the standard segments of the myocardium in the bullseye plot and the quantitative and/or qualitative information associated with each of the segments. Since bullseye plots play an important role in clinical decision-making, it is highly desirable to ensure that the standard myocardium segments described herein are accurately determined based on CMRI imagery and the bullseye plots are constructed to realistically reflect the anatomy of the human heart.

SUMMARY

Described herein are systems, methods and instrumentalities associated with generating bullseye plots based on CMRI imagery. A bullseyes plot generation apparatus as described herein may comprise one or more processors that are configured to obtain a plurality of first magnetic resonance (MR) slices based on a first cardiac magnetic resonance imaging (CMRI) scan taken along a short axis of a human heart and a second MR slice based on a second CMRI scan taken along a long axis of the human heart. The one or more processors may be further configured to determine one or more first landmark points associated with the human heart and a second landmark point associated with the human heart, and utilize the first and second landmark points to facilitate the generation of the bullseye plot. For instance, the one or more first landmark points may indicate a center of the LV and/or where the left ventricle (LV) of the human heart intersects with the right ventricle (RV) of the human heart, the second landmark point may indicate an apex of the myocardium, and the one or more processors may be configured to determine (e.g., using metadata associated with CMRI scan) respective projected locations of the first MR slices on the second MR slice. Based on the respective distances of these projected locations to the second landmark point, the one or more processors may arrange the first MR slices sequentially, e.g., in accordance with an original scan order of the first MR slices. The one or more processors may then determine a plurality of myocardial segments to be included in a bullseye plot based on the sequentially arranged first MR slices and the one or more first landmark points, and generate the bullseye plot using the plurality of myocardial segments.

In embodiments, the one or more processors of the bullseye generation apparatus may be configured to segment at least one of the first MR slices to identify the LV, the RV, and the myocardium using an artificial neural network. The one or more processors of the bullseye generation apparatus may also be configured to determine the first landmark points and/or the second landmark point using an artificial neural network. In embodiments, the first MR slices may be arranged sequentially from a basal slice to an apical slice based on the respective distances of the projected locations of the first MR slices to the apex of the myocardium, where the basal slice may correspond to a projected location that has a longest distance from the apex and the apical slice may correspond to a projected location that has a shortest distance from the apex. In embodiments, the one or more processors of the bullseye generation apparatus may also be configured to determine a direction of the first CMRI scan based on the respective distances of the projected locations of the first MR slices to the apex of the myocardium.

BRIEF DESCRIPTION OF THE DRAWINGS

A more detailed understanding of the examples disclosed herein may be had from the following description, given by way of example in conjunction with the accompanying drawing.

DETAILED DESCRIPTION

The present disclosure is illustrated by way of example, and not by way of limitation, in the figures of the accompanying drawings.

Figure 1B:
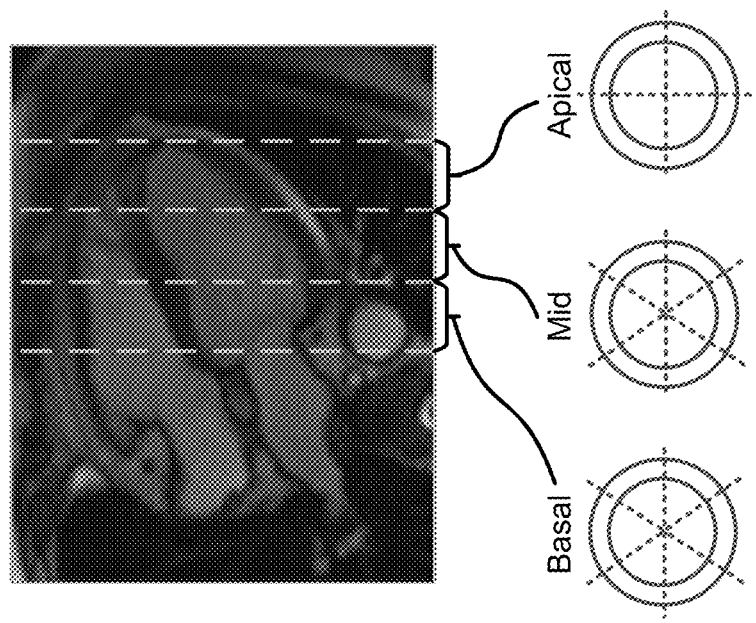
FIG. 1A and FIG. 1B are diagrams illustrating an example multi-segment bullseye plot of a myocardium and an example way of obtaining the segments of the bullseye plot.
Figure 1A:
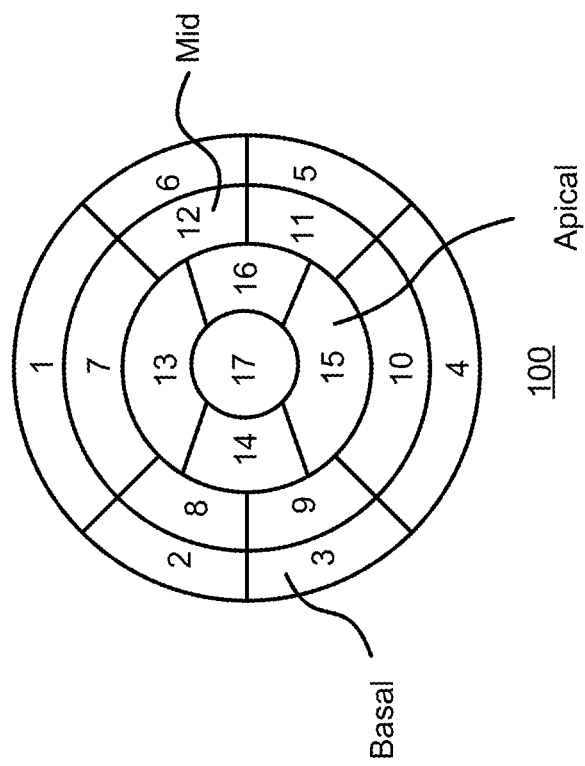

FIG. 1A illustrates an example bullseye plot 100 of a human heart and FIG. 1B illustrates ways of dividing a myocardium into the segments included in the bullseye plot 100. As shown, the bullseye plot 100 may include seventeen segments. Sixteen of the seventeen segments may each belong to a basal section of the myocardium, a middle (or mid) section of the myocardium, or an apical section of the myocardium. For example, the basal section may include six segments labeled 1-6, respectively, the middle section may also include six segments labeled 7-12, respectively, and the apical section may include four segments labeled 13-16, respectively. In addition, the bullseye plot 100 may also include a 17th segment that may correspond to an apex of the heart such as an apex of the myocardium.

Figure 2:
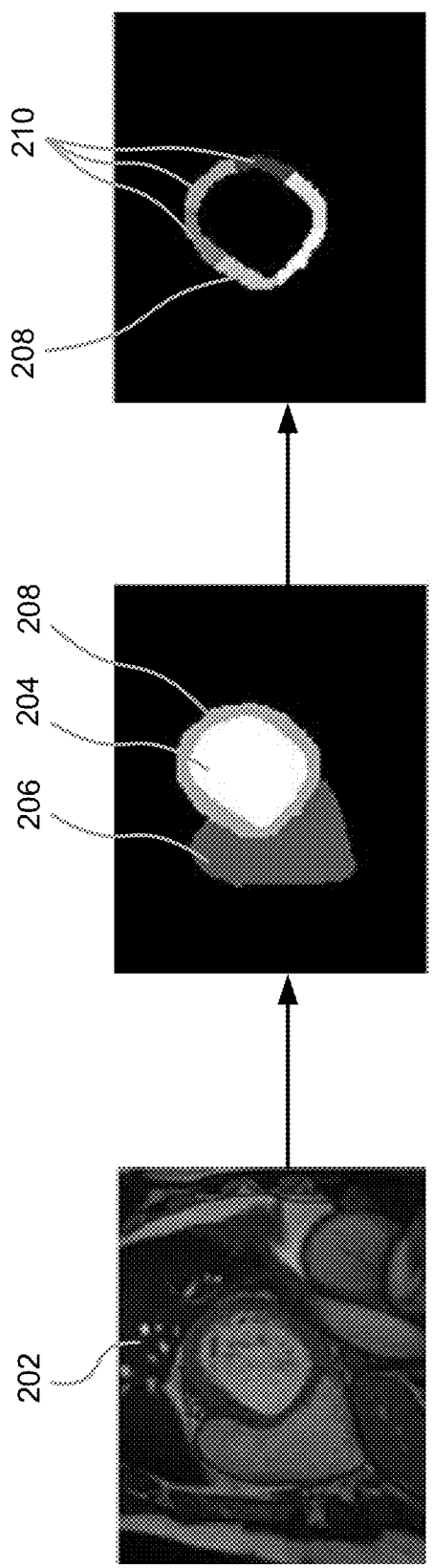
FIG. 2 is a diagram illustrating an example of segmenting a cardiac image and determining a plurality of myocardium segments that may be included in a bullseye plot.

The bullseye plot 100 may be generated based on imagery of the heart generated during different phases of a cardiac cycle including, for example, an end-diastole (ED) phase and/or an end-systole (ES) phase. FIG. 2 illustrates example techniques that may be employed by a bullseye plot generation apparatus described herein to construct a bullseye plot (e.g., the bullseye plot 100) based on imagery of the heart. The imagery may be obtained from one or more magnetic resonance imaging (MRI) scans of the heart and may include a plurality of magnetic resonance (MR) slices derived from the MRI scans. For instance, the MR slices may include a first plurality of slices derived from a first MRI scan taken along a short axis of the human heart. The MR slices may also include a second plurality of MR slices derived from a second MRI scan taken along a long axis of the human heart. When described herein, the short axis of the heart may be an axis that aligns the base of the heart and the apex of the heart, and the long axis of the heart may be an axis that is perpendicular to the short axis of the heart.

As shown in FIG. 2, the bullseye plot generation apparatus may obtain the first plurality of MR slices that may include a MR slice 202 taken along the short axis of the heart. The MR slice 202 may include multiple MM images of the heart (e.g., in the form of a movie) that are taken over a time period (e.g., one or more cardiac cycles). Each of the MRI images in the MR slice 202 may include a visual representation of all or a part of the left ventricle (LV), the right ventricle (RV), the myocardium, the left atrium, and/or the right atrium. From these images and the visual representations of the heart contained therein, the bullseye plot generation apparatus may identify (e.g., segment) the LV 204, the RV 206, and/or the myocardium 208 and further divide the myocardium 208 into multiple segments that may then be used to construct the bullseye plot shown in FIG. 1A. For example, the MR slice 202 may include visual representations of the basal section of the myocardium 208 and the bullseye plot generation apparatus may be configured to segment the myocardium 208 from the images included in the MR slice 202 and further divide the myocardium 208 into segments 210 (e.g., represented by different shades of colors in FIG. 2) that correspond to segments 1-6 of the bullseye plot in FIG. 1A. Likewise, the bullseye plot generation apparatus may also be configured to segment and divide the middle and apical sections of the myocardium 208 (e.g., into six and four segments, respectively) based on MR slices that represent those sections of the myocardium 208.

Figure 3:
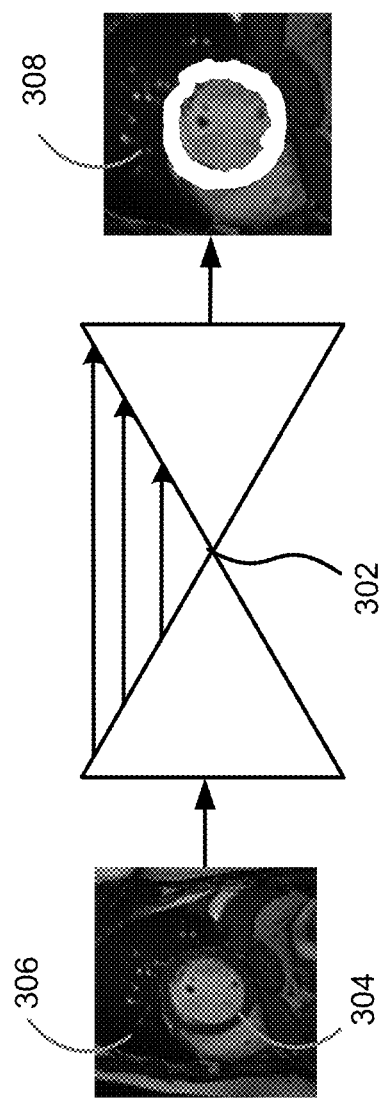
FIG. 3 is a block diagram illustrating an example of segmenting a cardiac image to identify a myocardium in the image.

The bullseye generation apparatus may include an artificial neural network trained to perform the segmentation tasks described herein. FIG. 3 shows an example segmentation neural network 302 that may be implemented by the bullseye generation apparatus to segment a myocardium 304 from an image 306 of the human heart (e.g., to delineate the myocardium 304 in the image 306). As described herein, the image 306 may be an MRI image of the heart included in a MR slice (e.g., produced by a CMRI). The image 306 may include a plurality of pixels with respective characteristics (e.g., varying brightness, contrast, intensity, gradient, etc.). The segmentation neural network 302 may be a convolutional neural network (CNN) such as a deep convolutional neural network that has been trained to identify one or more parts (e.g., one or more pixels) of the image 306 as belonging to the myocardium 304 and indicate the myocardium (e.g., the location and/or boundaries of the myocardium), for example, via a segmentation map or a segmentation mask. The segmentation neural network 302 may include one or more convolutional layers, one or more pooling layers, and/or one or more fully connected layers. Each of the convolutional layers may include a plurality of kernels or filters configured to identify specific features (e.g., keypoints) or patterns in the image 306. The kernels or filters may be associated with respective weights that may be learned via a training process. The convolution operations of each convolutional layer may be followed by batch normalization and/or activation (e.g., using a rectified linear unit (ReLU) function) before the output of one convolutional layer (e.g., in the form of a feature map) is provided as an input to the next convolutional layer. The feature maps generated by the convolutional layers may be down-sampled through the one or more pooling layers of the segmentation neural network 302 (e.g., using a 2×2 window and a stride of 2), for example, to reduce the redundancy and/or dimension of the features (e.g., by a factor of 2) identified in the image 306.

The down-sampled features may subsequently be up-sampled by the segmentation neural network 302, for example, via a series of transposed convolution operations (e.g., using 3×3 transposed convolutional kernels with a stride of 2) to recover the details associated with the identified features. One or more dense feature maps may be derived based on these operations, which may indicate the visual characteristics of various areas or pixels of the image 306. Based on these visual characteristics, a subset of the areas or pixels of the image 306 may be classified (e.g., via a fully connected layer of the segmentation neural network 302) as belonging to the myocardium 304 and a segmentation mask 308 may be generated to indicate the classification and/or segmentation. The segmentation neural network 302 may learn the visual characteristics of the myocardium from a training dataset that may comprise a large number of MRI images of the human heart and may acquire the parameters of the segmentation neural network 302 (e.g., the weights described herein) based on a gradient descent associated with a loss function that represents the difference between a segmentation estimated by the neural network and a ground truth (e.g., an annotated area of the myocardium) for the segmentation. Training of the segmentation neural network 302 will be described in greater detail below. Examples of a neural network that may be trained to perform a segmentation task can be found in commonly assigned U.S. patent application Ser. No. 16/905,115, filed Jun. 18, 2020, entitled "Systems and Methods for Image Segmentation" and U.S. patent application Ser. No. 17/014,594, filed Sep. 8, 2020, entitled "Hierarchical Systems and Methods for Image Segmentation," the disclosures of which are hereby incorporated by reference in their entireties.

Although not shown in FIG. 3, the segmentation neural network 302 may also be trained to segment (e.g., simultaneous to the segmentation of the myocardium) other parts of the human heart such as the LV and the RV based on the image 306. Alternatively, or in addition, the bullseye plot generation apparatus described herein may implement additional neural networks configured to segment those other parts (e.g., the LV or RV) of the heart. These additional neural networks may have similar structures as the segmentation neural network 302, but may be trained (e.g., using different training datasets than the segmentation neural network 302) to specifically identify the other parts of the heart.

Figure 4:
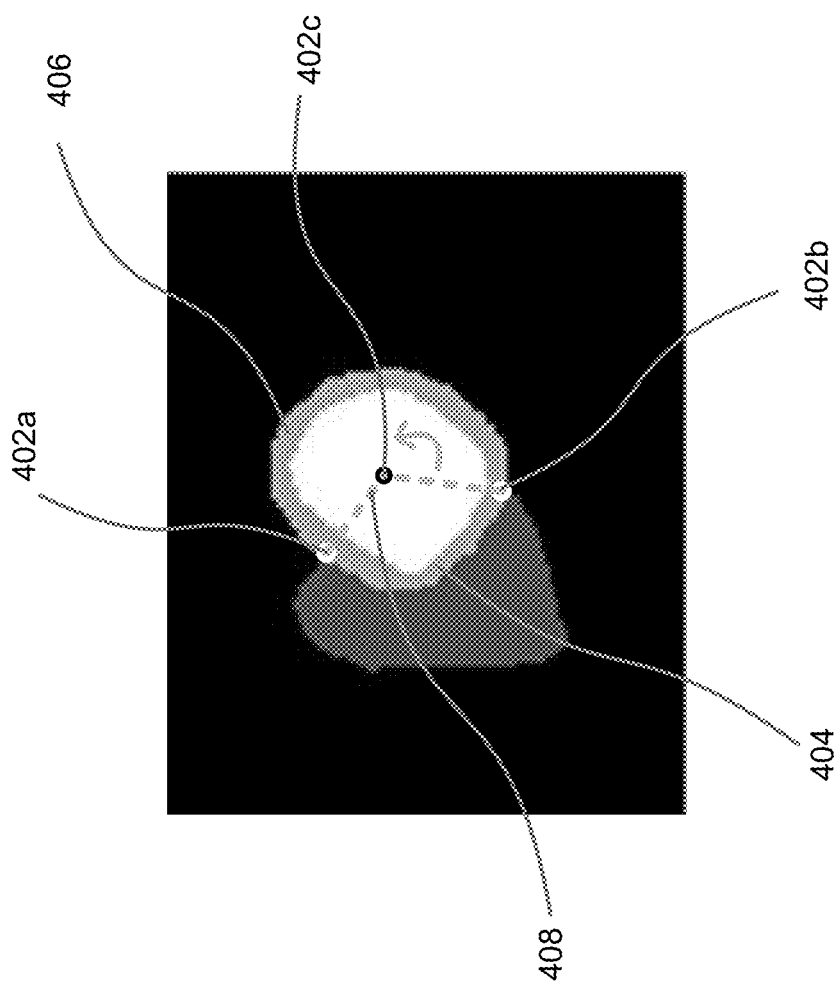
FIG. 4 is a diagram illustrating an example of determining multiple landmark points in a segmentation mask and obtaining a plurality of myocardial segments based on the landmark points.

The bullseye plot generation apparatus described herein may be further configured to determine one or more first landmark points associated with the human heart based on the first plurality of MR slices and one or more second landmark points associated with the human heart based on in the second plurality of MR slices, and use the first and second landmark points to facilitate the generation of a bullseye plot. FIG. 4 shows an example of utilizing landmark points 402a, 402b, and 402c to divide the myocardium to obtain the segments of a bullseye plot. In the example, the landmark points 402a and 402b may represent points where the RV intersects the LV (e.g., at the anterior and inferior LV myocardium) and the landmark point 402c may represent a center of the LV. The landmark points 402a and 402b may divide the myocardium 406 into two parts, 404 and 406, where part 404 may be shorter than part 406. As such, to obtain the segments of the basal section and the middle section of the myocardium for a bullseye plot, the bullseye plot generation apparatus may be configured to divide (e.g., equally) the shorter part 404 into two segments and the longer part 406 into four segments (e.g., corresponding to segments 1-6 and segments 7-12 shown in FIG. 2). To obtain the segments of the apical section of the myocardium for the bullseye plot, the bullseye plot generation apparatus may be configured to treat the shorter part 404 as one myocardial segment and divide (e.g., equally) the longer part 406 into three segments (e.g., corresponding to segments 13-16 shown in FIG. 1A).

The bullseye plot generation apparatus may be configured perform the division of the myocardium further utilizing the landmark point 402c. For instance, the bullseye plot generation apparatus may be configured to draw a line 408 (e.g., an imaginary line) between the landmark point 402c and either of the landmark points 402a and 402b and rotate the line 408 at equal angular steps around the myocardium to obtain the segments for the bullseye plot. Such angular steps may be, for example, 60 degrees if the myocardium is to be divided into six segments (e.g., for the basal section and the middle section) and 90 degrees if the myocardium is to be divided into four segments (e.g., for the apical section).

In example implementations, the bullseye plot generation apparatus may be configured to identify one or more of the landmark points described herein (e.g., such as the landmark points 402a and 402b) using a landmark detection neural network. The landmark detection neural network may include a convolutional neural network such as a deep convolutional neural network. The network may include one or more convolutional layers, one or more pooling layers, and/or one or more fully connected layers. Each of the convolutional layers may include a plurality of kernels or filters configured to identify specific features (e.g., keypoints) or patterns in an input image. The kernels or filters may be associated with respective weights that may be learned via a training process. The convolution operations performed via each of the convolutional layers may be followed by batch normalization and/or activation (e.g., using a rectified linear unit (ReLU) function) before the output of the convolutional layer (e.g., in the form of a feature map) is provided to the next convolutional layer and used to extract higher level or higher order features from the input image. The feature maps generated by the convolutional layers may be down-sampled through the one or more pooling layers of the landmark detection neural network (e.g., using a 2×2 window and a stride of 2), for example, to reduce the redundancy and/or dimension of the features (e.g., by a factor of 2) identified in the input image. The down-sampled features may subsequently be up-sampled by the network, for example, via a series of transposed convolution operations (e.g., using 3×3 transposed convolutional kernels with a stride of 2) to recover the details associated with the identified features. One or more dense feature maps may be derived based on these operations to indicate the visual characteristics of various areas or pixels of the input image. Based on these visual characteristics, the landmark detection neural network may identify the area(s) or pixel(s) of the input image that corresponds to the landmark point(s) of interest (e.g., based on matching visual characteristics) and determine respective locations of the landmark point(s) accordingly. The landmark detection neural network may learn the visual characteristics of the landmark point(s) from a training dataset that may comprise a large number of MRI images of the human heart and may acquire the parameters of the network (e.g., the weights described herein) based on a gradient descent associated with a loss function that represents the difference between landmark locations estimated by the network and a ground truth (e.g., annotated locations of the landmark points) for the locations. The training of the landmark detection neural network will be described in greater detail below.

In example implementations, the bullseye plot generation apparatus may be configured to identify one or more of the landmark points described herein based on a segmentation mask or a segmentation map already generated for a part of the human heart. For instance, the bullseye plot generation apparatus may obtain a segmentation mask of the LV using a segmentation neural network (e.g., such as the segmentation neural network 302 described herein) and determine a center of the LV (e.g., the landmark points 402c) based on pixels that have been identified as being parts of the LV. For example, the bullseye plot generation apparatus may determine the center of the LV based on an average (e.g., a weighted average) of the coordinates of the pixels that are located on an endocardial boundary or an epicardial boundary.

To generate a bullseye plot based on a CMRI scan, the bullseye plot generation apparatus may need to ascertain a direction (e.g., orientation) of the CMRI scan and/or organize the MR slices obtained therefrom (e.g., the short-axis MR slices described herein) sequentially (e.g., in accordance with the order in which the MR slices are generated during the scan or reverse to the order in which the MR slices are generated during the scan). In some circumstances, however, the direction of a CMRI scan may not be known to the bullseye plot generation apparatus and/or the MR slices may not be organized sequentially (e.g., in accordance with or reverse to the scan order of the MR slices). Accordingly, responsive to obtaining a plurality of MR slices (e.g., the short-axis MR slices) based on a CMRI scan, the bullseye plot generation apparatus may be configured to arrange (e.g., re-arrange) the MR slices sequentially, for example, in an order that complies with the scan order of the MR slices. The bullseye plot generation apparatus may also be configured to determine a direction (e.g., orientation) of the CMRI scan based on the re-arranged MR slices. The bullseye plot generation apparatus may accomplish these tasks by determining respective projected locations of the short-axis MR slices on a long-axis MR slice and order the short-axis slices based on a sequential order of respective distances of the projected locations to a landmark point on the long-axis MR slice.

Figure 5:
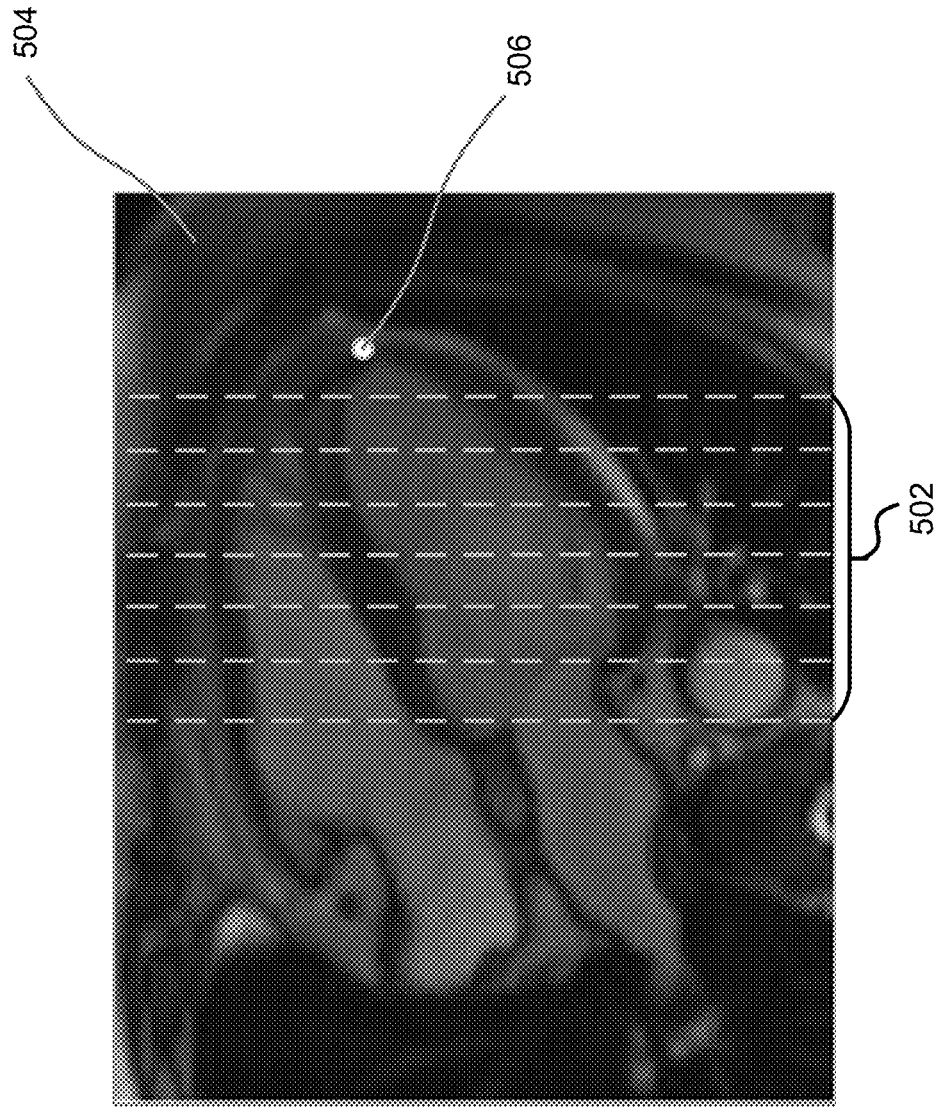
FIG. 5 is a diagram illustrating an example of arranging short-axis MR slices based on a sequential order of corresponding long-axis MR images.

FIG. 5 illustrates an example of arranging a plurality of short-axis MR slices and/or determining the direction (e.g., orientation) of a CMRI scan based on projected locations 502 of the short-axis MR slices on a long-axis MR slice 504 and/or a landmark point 506. As described herein, the plurality of short-axis MR slices may be generated during a CMRI scan in accordance with a specific scan order (e.g., from basal to apical or vice versa). When provided to the bullseye plot generation apparatus described herein, however, the short-axis MR slices may become disorganized and may no longer be in a sequential order (e.g., in accordance with the original scan order). To put the short-axis MR slices back in a sequential order (e.g., in accordance with their original scan order), the bullseye plot generation apparatus may determine the locations 502 where the short-axis MR slices (e.g., the respective image planes of the short-axis MR slices) intersect with a long-axis MR slice of the heart and utilize the distances of the locations 502 to the landmark point 506 to determine the sequential order of the short-axis MR slices.

The bullseye plot generation apparatus may select the long-axis MR slice 504 (e.g., a middle slice) from a plurality of long-axis MR slices obtained by the bullseye plot generation apparatus and determine respective image planes that correspond to the short-axis MR slices and the long-axis MR slice 504 based on metadata (e.g., header information such as DICOM header information) associated with the short and/or long-axis MR slices. The metadata may be obtained by the bullseye plot generation apparatus, for example, together with the short and/or long-axis MR slices, or separately from the short and/or long-axis MR slices. Responsive to obtaining the metadata, the bullseye plot generation apparatus may extract information regarding slice/image orientations, slice/image positions, slice/image pixel resolutions, etc., from the metadata. The bullseye plot generation apparatus may then use the extracted information to determine respective plane equations for the short-axis MR slices and the long-axis MR slice. Each of these equations may include a norm vector that is perpendicular to the corresponding slice/image plane and a sample point on the slice/image plane (e.g., the norm vector and sample point may define the slice/image plane). As such, using respective norm vectors and sample points associated with a short-axis MR slice and the long-axis MR slice 504, the bullseye plot generation apparatus may determine a projected location 502 of the short-axis MR slice on the long-axis slice 504 (e.g., the projected location may correspond to an intersection line of the short-axis MR slice and the long-axis MR slice 504). The bullseye plot generation apparatus may then determine the respective distances of these projected locations 502 from the landmark point 506 and arrange (e.g., order) the short-axis MR slices based on the distances. For example, given short-axis MR slices S1, S4, S3, and S2, the bullseye plot generation apparatus may determine, based on metadata information associated with the short-axis slices and/or the long-axis slice 504, that S1, S4, S3, and S2 may be projected onto the long-axis slice 504 at locations L1, L4, L3, and L2, respectively, and that the distances of those locations from the landmark point 506 are D1, D4, D3, and D2, respectively. The bullseye plot generation apparatus may further determine that the values of the distances from the landmark point 506, in a descending order, is D1, D2, D3, and D4. As such, the bullseye plot generation apparatus may determine that the sequential order of the short-axis MR slices (e.g., in accordance with their original scan order) should be S1, S2, S3, and S4, where S1 may correspond to a slice closer to the basal section of the myocardium (e.g., S1 may be a basal slice), and S4 may represent a slice closer to the apical section of the myocardium (e.g., S4 may be an apical slice).

The bullseye plot generation apparatus may also be able to determine a direction (e.g., orientation) of the CMRI scan based on the projected locations 502 of the short-axis MR slices on the long-axis MR slice 504. In embodiments, if the first short-axis MR slice has a projected location on the long-axis MR slice 504 that is at a greater distance from the landmark point 506 than the last short-axis MR slice, the bullseye plot generation apparatus may determine that the scan direction is from basil to apical. In embodiments, the bullseye plot generation apparatus may determine the scan direction based on an average distance. For example, if the average distance of the projected locations of slices 1-5 from the landmark point 506 is larger than the average distance of the projected locations of slices 6-10 from the landmark point 506, the bullseye plot generation apparatus may decide that the scan is from basal to apical, or vice versa.

The bullseye plot generation apparatus may determine the landmark point 506 and/or one or more other long-axis landmark points (e.g., points that indicate a mitral annulus level) based on long-axis MR slices obtained from the CMRI scan. The landmark point 506 may be, for example, an apex of the myocardium. The bullseye plot generation apparatus may be configured to determine the landmark point 506 (e.g., the apex) and/or the other long-axis landmark points using the landmark detection neural network described herein or using a separate neural network that has a similar structure to the landmark detection neural network but has been trained differently (e.g., with a different training dataset and/or ground truth) to specifically identify the long-axis landmark points. For example, the bullseye plot generation apparatus may be configured to determine the long-axis landmark points using a convolutional neural network such as a deep convolutional neural network that include one or more convolutional layers, one or more pooling layers, and/or one or more fully connected layers. Using these layers, the convolutional neural network may extract visual features from the long-axis slices or images and identify areas or pixels that match the characteristics of the one or more long-axis landmark points that the neural network has learned from training.

Figure 6:
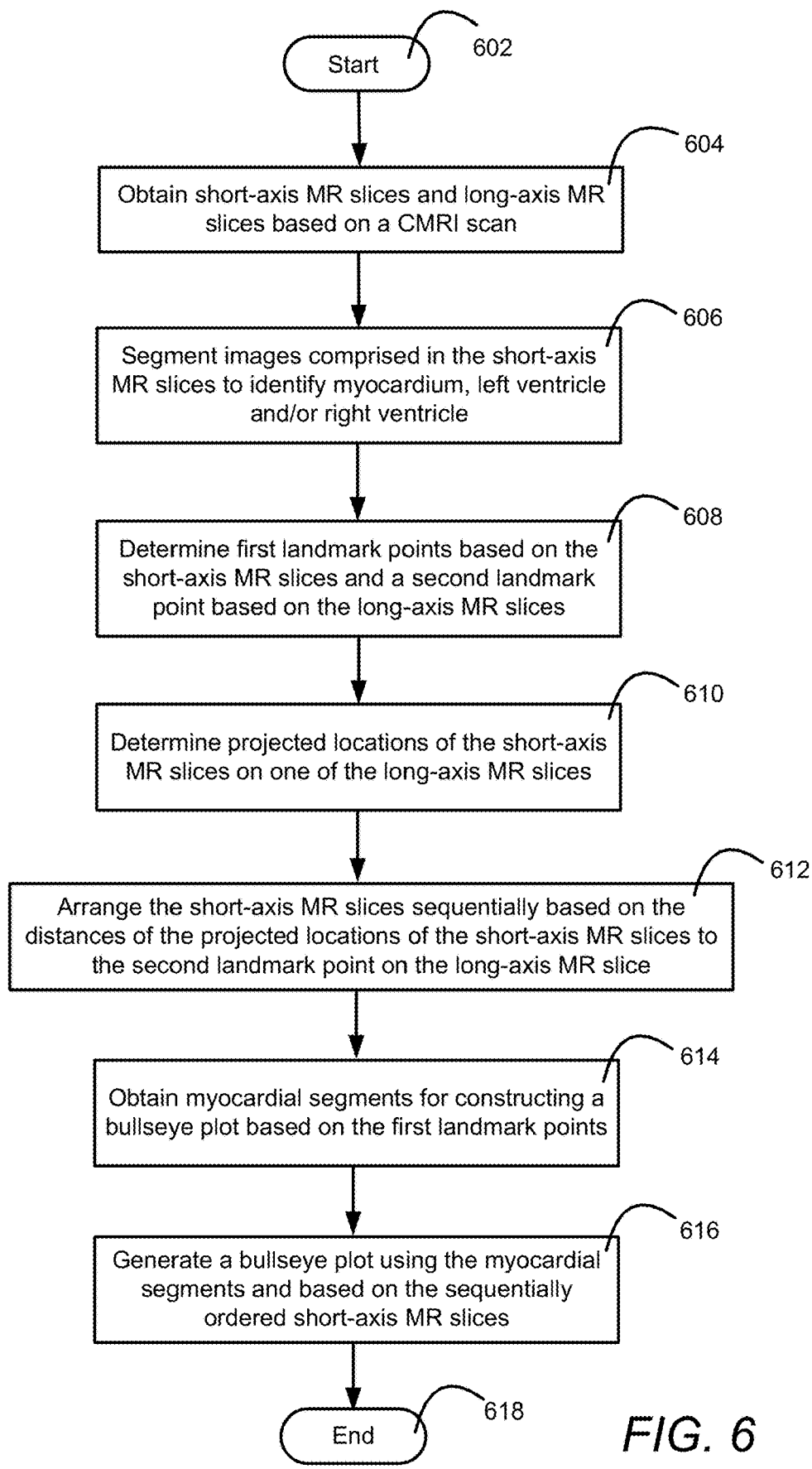
FIG. 6 is a flow diagram illustrating example operations of a bullseye plot generation apparatus described herein.

FIG. 6 illustrates example operations that may be performed by the bullseye plot generation apparatus described herein. The operations may start at 602 and the bullseye plot generation apparatus may obtain short-axis MR slices and long-axis MR slices at 604 based on a CMRI scan performed for a patient. At 606, the bullseye plot generation apparatus may segment (e.g., using a segmentation neural network described herein) the images comprised in the short-axis MR slices to identify the myocardium, the left ventricle, and/or the right ventricle in the images. At 608, the bullseye plot generation apparatus may determine (e.g., using a landmark detection neural network) first landmark points such as the landmark points 402a-402c shown in FIG. 4 based on the short-axis MR slices and/or the segmentation. The bullseye plot generation apparatus may also determine a second landmark point such as the apex 506 shown in FIG. 5 based on the long-axis MR slices. At 610, the bullseye plot generation apparatus may determine respective projected locations of the short-axis MR slices on one of the long-axis MR slices based on, e.g., metadata information associated with the CMRI scan. As described herein, these projected locations may be distanced sequentially from an identified landmark point (e.g., the apex of the myocardium) on the long-axis slice. Therefore, the bullseye plot generation apparatus may, at 612, arrange the short-axis MR slices sequentially based on the respective distances of the projected locations on the long-axis slice from the identified landmark point. At 614, the bullseye plot generation apparatus may divide the myocardium depicted in the short-axis MR slices into segments based on the first landmark points identified at 608, for example, as illustrated by FIG. 4. The bullseye plot generation apparatus may then generate a bullseye plot (e.g., a sixteen-segment or seventeen-segment bullseye plot) based on the myocardial segments and the sequentially ordered short-axis MR slices, before the bullseye plot generation apparatus ends the operations at 618.

Example operations have been depicted and described herein with a specific order. It should be noted, however, that these operations may be performed in a different order, concurrently, and/or together with other operations not presented or described herein. Further, it should be noted that not all operations that the bullseye plot generation apparatus is capable of performing are depicted and described herein, and not all illustrated operations are required to be performed by the bullseye plot generation apparatus.

Figure 7:
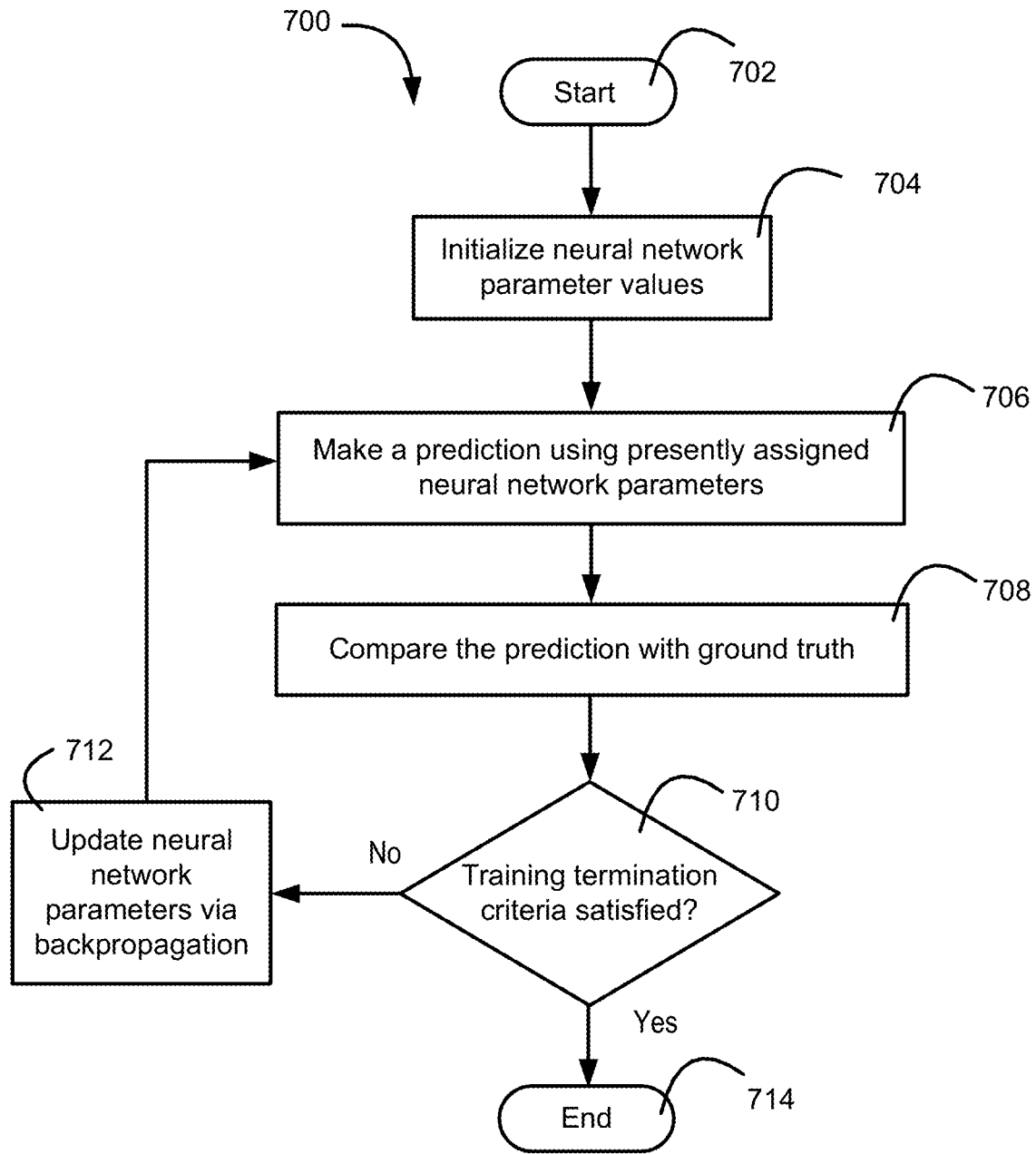
FIG. 7 is a flow diagram illustrating an example process for training a neural network that may be implemented by a bullseye plot generation apparatus described herein.

The neural networks described herein (e.g., the segmentation neural network, the landmark detection neural network, etc.) may be trained to optimize their parameters (e.g., weights associated with the layers of the neural networks) for performing the various identification, prediction, or estimation tasks described herein. The training may be conducted using a plurality of images of the human hearts and/or respective loss functions designed to guide the neural networks through the learning and/or optimization process. FIG. 7 illustrates an example process 700 for training a neural network described herein (e.g., the segmentation neural network and/or the landmark detection neural network described herein). The process 700 may start at 702 and, at 704, the neural network may initialize its operating parameters such as the weights associated with one or more filters or kernels of the neural network. The parameters may be initialized, for example, based on samples from one or more probability distributions or parameter values of another neural network with a similar architecture. At 706, the neural network may receive a training image of the human heart, process the image through the various layers of the neural network, and make a prediction for a target result (e.g., a segmentation mask of the myocardium, LV, or RV, a classification of a landmark point, etc.) using presently assigned parameters. At 708, the neural network may determine adjustments to be made to the presently assigned parameters based on a loss function and a gradient descent (e.g., a stochastic gradient decent) associated with the loss function. For example, the loss function may be implemented based on a mean squared error (MSE), a Dice ratio, a cross entropy, etc. between the prediction and a ground truth associated with the prediction (e.g., an annotation of the myocardium or the landmark point). At 710, the neural network may carry out the adjustments to the presently assigned parameters, for example, via a backpropagation process. At 712, the neural network may determine whether one or more training termination criteria are satisfied. For example, the neural network may determine that the training termination criteria are satisfied if the neural network has completed a pre-determined number of training iterations, if the difference between the predicted values and the ground truth values is below a predetermined threshold, or if the change in the value of the loss function between two training iterations falls below a predetermined threshold. If the determination at 712 is that the training termination criteria are not satisfied, the neural network may return to 706. If the determination at 712 is that the training termination criteria are satisfied, the neural network may end the training process 700 at 714.

Figure 8:
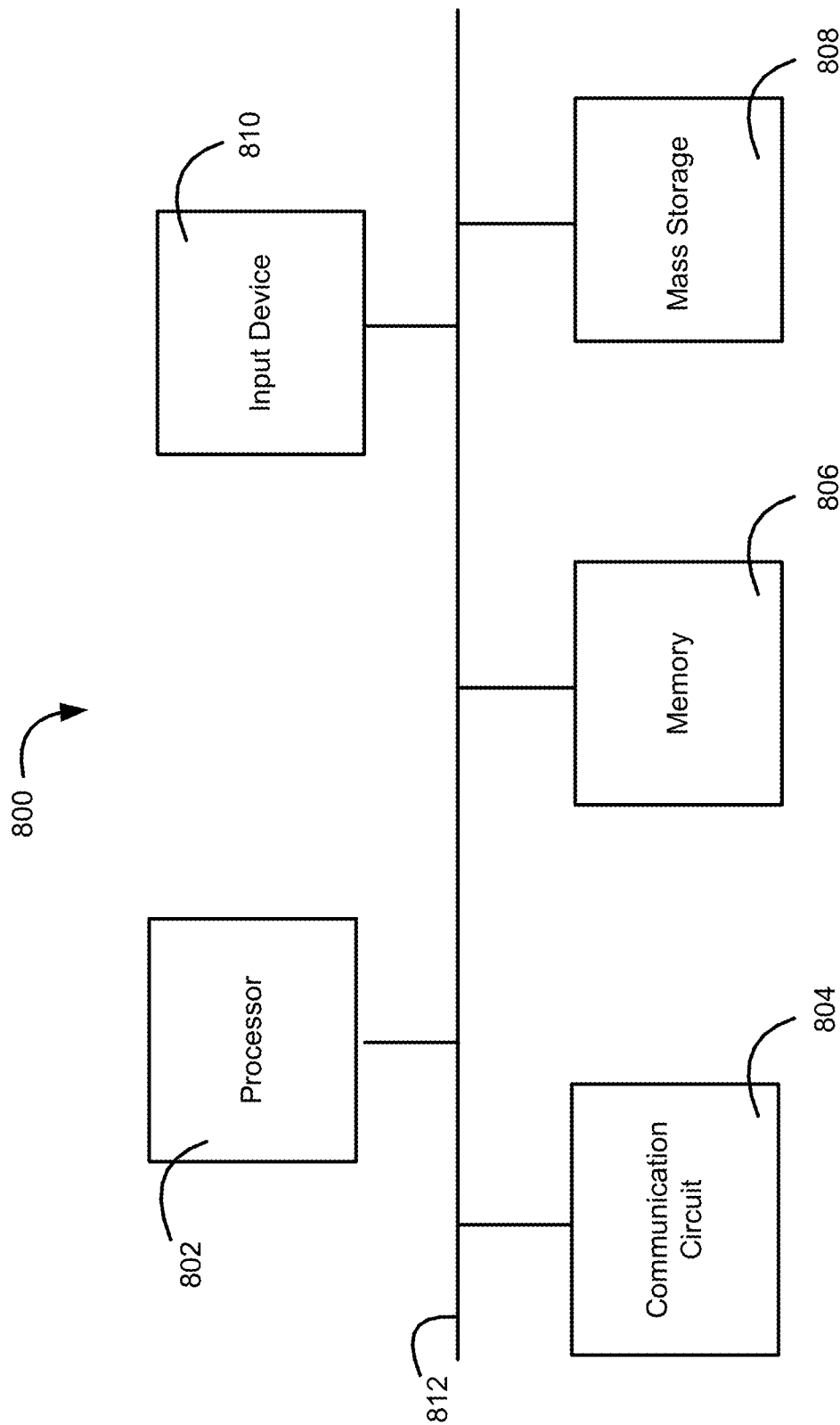
FIG. 8 is a block diagram illustrating example components of a bullseye plot generation apparatus described herein.

The bullseye plot generation apparatus described herein may be implemented using one or more processors, one or more storage devices, and/or other suitable accessory devices such as display devices, communication devices, input/output devices, etc. FIG. 8 is a block diagram illustrating an example bullseye plot generation apparatus 800 as described herein. As shown, the bullseye plot generation apparatus 800 may include a processor 802, which may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. The bullseye plot generation apparatus 800 may further include a communication circuit 804, a memory 806, a mass storage device 808, an input device 810, and/or a communication link 812 (e.g., a communication bus) over which the one or more components shown in FIG. 8 may exchange information. The communication circuit 804 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 806 may include a storage medium configured to store machine-readable instructions that, when executed, cause the processor 802 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EEPROM)), flash memory, and/or the like. The mass storage device 808 may include one or more magnetic disks such as one or more internal hard disks, one or more removable disks, one or more magneto-optical disks, one or more CD-ROM or DVD-ROM disks, etc., on which instructions and/or data may be stored to facilitate the operation of the processor 802. The input device 810 may include a keyboard, a mouse, a voice-controlled input device, a touch sensitive input device (e.g., a touch screen), and/or the like for receiving user inputs to the bullseye plot generation apparatus 800.

It should be noted that the bullseye plot generation apparatus 800 may operate as a standalone device or may be connected (e.g., networked or clustered) with other computation devices to perform the functions described herein. And even though only one instance of each component is shown in FIG. 8, a skilled person in the art will understand that the bullseye plot generation apparatus 800 may include multiple instances of one or more of the components shown in the figure. Furthermore, although the examples are described herein with reference to various types of neural networks, various types of layers, and/or various tasks being performed by certain types of neural networks or layers, those references are made merely for illustration purposes and not meant to limit the scope of the disclosure. And while this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. An apparatus configured to generate a bullseye plot, comprising:
   one or more processors configured to:
   obtain a plurality of first magnetic resonance (MR) slices based on a first cardiac magnetic resonance imaging (CMRI) scan of a human heart taken along a short axis of the human heart;
   obtain a second MR slice based on a second CMRI scan of the human heart taken along a long axis of the human heart;
   determine one or more first landmark points associated with the human heart based on the first MR slices, wherein the one or more first landmark points indicate where a left ventricle (LV) of the human heart intersects a right ventricle (RV) of the human heart;
   determine a second landmark point associated with the human heart based on the second MR slice;
   determine respective projected locations of the first MR slices on the second MR slice;
   arrange the first MR slices sequentially based on respective distances of the projected locations of the first MR slices on the second MR slice to the second landmark point;
   determine a plurality of myocardial segments based on the sequentially arranged first MR slices and the one or more first landmark points; and
   generate the bullseye plot based on the plurality of myocardial segments.

2. The apparatus of claim 1, where the one or more first landmark points further indicate a center of the LV.

3. The apparatus of claim 2, wherein the one or more processors are configured to determine a first section of a myocardium and a second section of the myocardium based on where the LV intersects with the RV and divide the first section of the myocardium into a first set of one or more equal segments and the second section of the myocardium into a second set of one or more equal segments based on the center of the LV and where the LV intersects with the RV.

4. The apparatus of claim 1, wherein the one or more processors are configured to segment at least one of the first MR slices to identify the LV, the RV, and a myocardium in the at least one of the first MR slices, and determine the one or more first landmark points based on the segmentation.

5. The apparatus of claim 4, where the one or more processors are configured to segment the at least one of the first MR slices to identify the LV, the RV, and the myocardium using an artificial neural network.

6. The apparatus of claim 1, wherein the second landmark point indicates an apex of a myocardium.

7. The apparatus of claim 6, wherein the one or more processors are configured to arrange the first MR slices from a basal slice to an apical slice based on the respective projected locations of the first MR slices on the second MR slice, the basal slice corresponding to a location on the second MR slice that has a longest distance from the apex, the apical slice corresponding to a location on the second MR slice that has a shortest distance from the apex.

8. The apparatus of claim 6, wherein the one or more processors are further configured to determine a direction of the first CMRI scan based on the respective projected locations of the first MR slices on the second MR slice to the second landmark point.

9. The apparatus of claim 1, wherein the one or more processors are configured to obtain metadata associated with the first MR slices and the second MR slice and determine the respective projected locations of the first MR slices on the second MR slice based on the metadata.

10. A method for generating a bullseye plot, the method comprising:
    obtaining a plurality of first magnetic resonance (MR) slices based on a first cardiac magnetic resonance imaging (CMRI) scan of a human heart taken along a short axis of the human heart;
    obtaining a second MR slice based on a second CMRI scan of the human heart taken along a long axis of the human heart;
    determining one or more first landmark points associated with the human heart based on the first MR slices, wherein the one or more first landmark points indicate where a left ventricle (LV) of the human heart intersects a right ventricle (RV) of the human heart;
    determining a second landmark point associated with the human heart based on the second MR slice;
    determining respective projected locations of the first MR slices on the second MR slice;
    arranging the first MR slices sequentially based on respective distances of the projected locations of the first MR slices on the second MR slice to the second landmark point;
    determining a plurality of myocardial segments based on the sequentially arranged first MR slices and the one or more first landmark points; and
    generating the bullseye plot based on the plurality of myocardial segments.

11. The method of claim 10, where the one or more first landmark points further indicate a center of the LV.

12. The method of claim 11, wherein determining the plurality of myocardial segments based on the sequentially arranged first MR slices and the one or more first landmark points comprises determining a first section of a myocardium and a second section of the myocardium based on where the LV intersects with the RV and dividing the first section of the myocardium into a first set of one or more equal segments and the second section of the myocardium into a second set of one or more equal segments based on the center of the LV and where the LV intersects with the RV.

13. The method of claim 10, wherein further comprising segmenting at least one of the first MR slices to identify the LV, the RV, and a myocardium in the at least one of the first MR slices, and determining the one or more first landmark points based on the segmentation.

14. The method of claim 13, where the at least one of the first MR slices is segmented using an artificial neural network.

15. The method of claim 10, wherein the second landmark point indicates an apex of a myocardium.

16. The method of claim 15, wherein the first MR slices are arranged from a basal slice to an apical slice based on the respective projected locations of the first MR slices on the second MR slice, the basal slice corresponding to a location on the second MR slice that has a longest distance from the apex, the apical slice corresponding to a location on the second MR slice that has a shortest distance from the apex.

17. The method of claim 15, further comprising determining a direction of the first CMRI scan based on the respective projected locations of the first MR slices on the second MR slice to the second landmark point.

18. The method of claim 10, further comprising obtaining metadata associated with the first MR slices and the second MR slice, wherein the respective projected locations of the first MR slices on the second MR slice are determined based on the metadata.

\* \* \* \* \*